(12) United States Patent
Takahashi et al.

(10) Patent No.: US 9,050,003 B2
(45) Date of Patent: Jun. 9, 2015

(54) RECONSTRUCTION COMPUTING DEVICE, RECONSTRUCTION COMPUTING METHOD, AND X-RAY CT APPARATUS

(75) Inventors: Hisashi Takahashi, Tokyo (JP); Taiga Goto, Tokyo (JP); Koichi Hirokawa, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 194 days.

(21) Appl. No.: 13/635,391

(22) PCT Filed: Mar. 29, 2011

(86) PCT No.: PCT/JP2011/057784
§ 371 (c)(1),
(2), (4) Date: Sep. 14, 2012

(87) PCT Pub. No.: WO2011/122613
PCT Pub. Date: Oct. 6, 2011

(65) Prior Publication Data
US 2013/0028500 A1    Jan. 31, 2013

(30) Foreign Application Priority Data
Mar. 30, 2010    (JP) .................... 2010-076956

(51) Int. Cl.
*G06K 9/00* (2006.01)
*A61B 6/03* (2006.01)
*A61B 6/00* (2006.01)
(Continued)

(52) U.S. Cl.
CPC ............ *A61B 6/032* (2013.01); *A61B 6/5205* (2013.01); *G06T 11/006* (2013.01); *A61B 6/06* (2013.01); *G06T 2211/424* (2013.01)

(58) Field of Classification Search
None
See application file for complete search history.

(56) References Cited

U.S. PATENT DOCUMENTS

| 5,963,211 A | 10/1999 | Oikawa et al. |
| 6,061,422 A | 5/2000 | Miyazaki et al. |
| 6,768,782 B1 | 7/2004 | Hsieh et al. |

(Continued)

FOREIGN PATENT DOCUMENTS

| JP | 11-9589 | 1/1999 |
| JP | 2003-153893 | 5/2003 |

(Continued)

OTHER PUBLICATIONS

International Search Report in connection with PCT/JP2011/057784.

*Primary Examiner* — Jon Chang
*Assistant Examiner* — Oneal R Mistry
(74) *Attorney, Agent, or Firm* — Cooper & Dunham LLP

(57) ABSTRACT

In order to provide a reconstruction computing device, a reconstruction computing method, and an X-ray CT apparatus capable of improving the image quality while reducing the amount of computation when reconstructing an X-ray CT image using an iterative method, a reconstruction computing device 45 divides an initial image 50 reconstructed using an analytical method such as an FBP method into a bed region 51, an object region 52, and the other air region 53, sets reconstruction conditions including at least convergence conditions and a pixel size for each of the divided regions, updates estimation images by performing an iterative process, and fixes estimation images or forward projection data of a subset satisfying the convergence conditions until other subsets satisfy the convergence conditions.

7 Claims, 14 Drawing Sheets

(51) Int. Cl.
  *G06T 11/00* (2006.01)
  *A61B 6/06* (2006.01)

(56) References Cited

U.S. PATENT DOCUMENTS

| | | | |
|---|---|---|---|
| 8,233,690 B2 * | 7/2012 | Ng et al. | 382/131 |
| 2006/0013459 A1 | 1/2006 | Katscher et al. | |
| 2007/0165769 A1 | 7/2007 | Goto et al. | |
| 2007/0217566 A1 | 9/2007 | Chen et al. | |
| 2007/0297656 A1 * | 12/2007 | DeMan et al. | 382/128 |
| 2008/0205729 A1 | 8/2008 | Ziegler et al. | |
| 2009/0190814 A1 | 7/2009 | Bouman et al. | |
| 2009/0202036 A1 * | 8/2009 | Ziegler et al. | 378/19 |
| 2010/0054564 A1 * | 3/2010 | Vija et al. | 382/131 |
| 2010/0316270 A1 | 12/2010 | Erhard et al. | |
| 2011/0007958 A1 * | 1/2011 | Salomon et al. | 382/131 |
| 2011/0129057 A1 * | 6/2011 | Paul et al. | 378/4 |
| 2011/0142313 A1 * | 6/2011 | Pack et al. | 382/131 |

FOREIGN PATENT DOCUMENTS

| | | |
|---|---|---|
| JP | 3527796 | 2/2004 |
| JP | 2005-521881 | 7/2005 |
| JP | 2007-244871 | 9/2007 |
| JP | 2008-6288 | 1/2008 |
| JP | 2008-532683 | 8/2008 |
| JP | 2009-172380 | 8/2009 |
| JP | 2010-4959 | 1/2010 |
| WO | WO 2005/072613 | 8/2005 |
| WO | WO 2008062415 A3 * | 3/2009 |
| WO | WO2009/083866 | 7/2009 |
| WO | WO 2010/016425 A1 | 2/2010 |

\* cited by examiner

F I G . 4
(a)
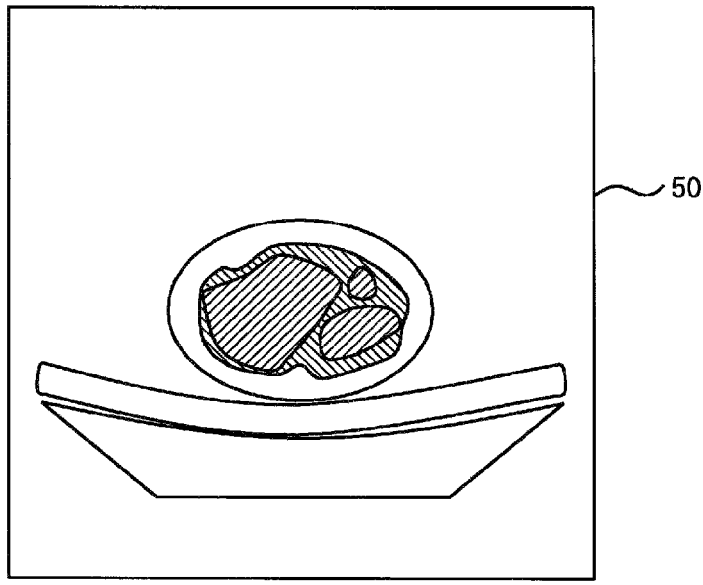
(b)
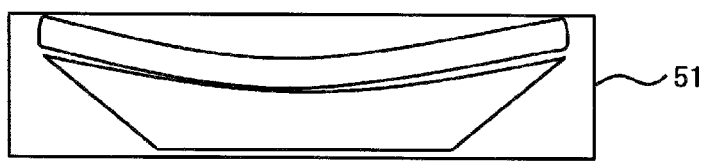
(c)
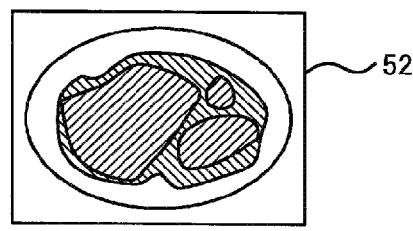

FIG. 5
(a)
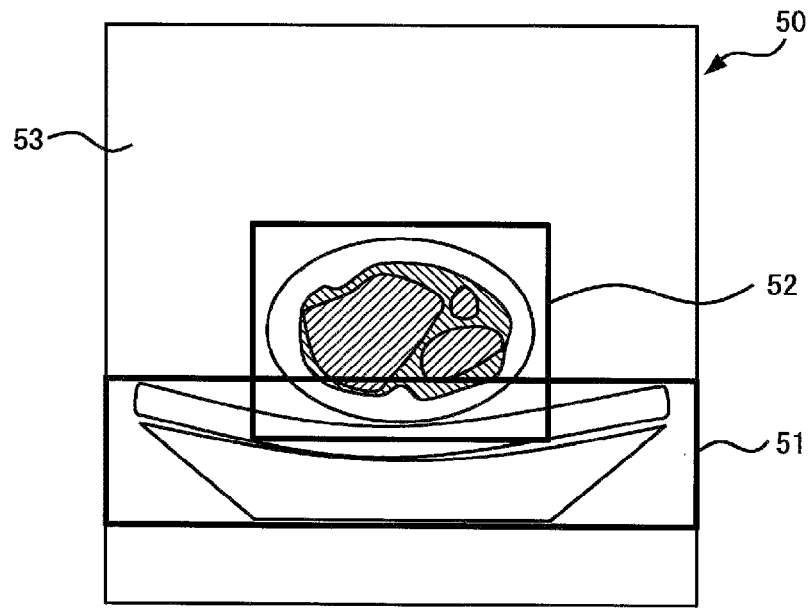
(b)
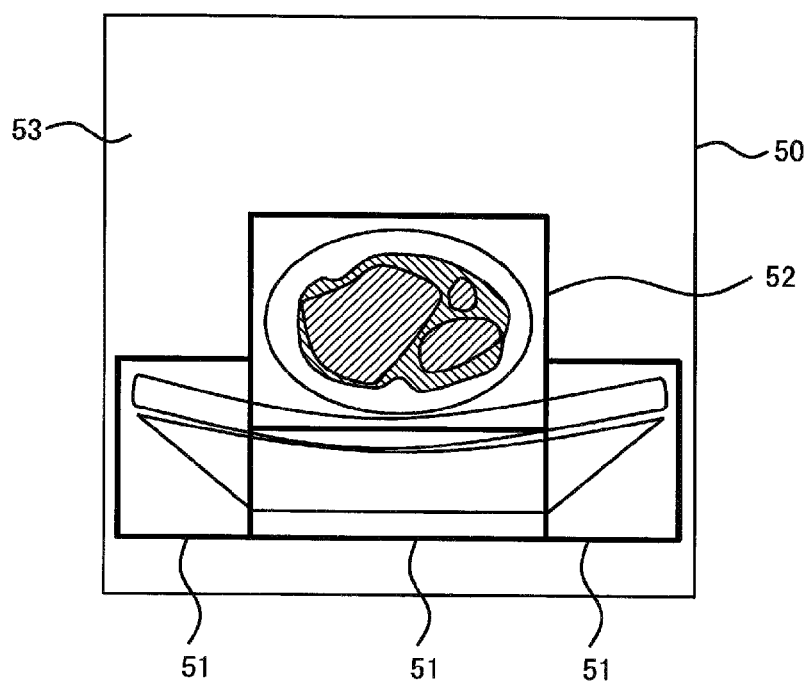

FIG. 6
(a)
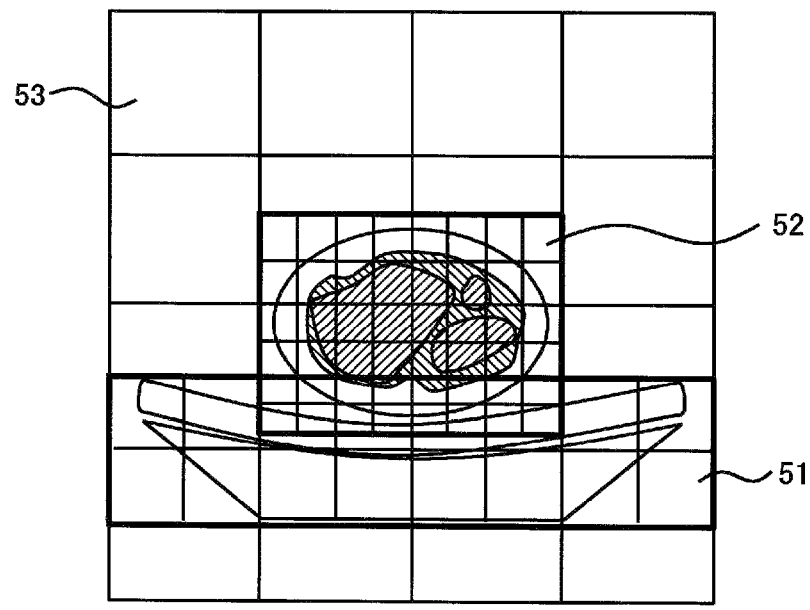
(b)
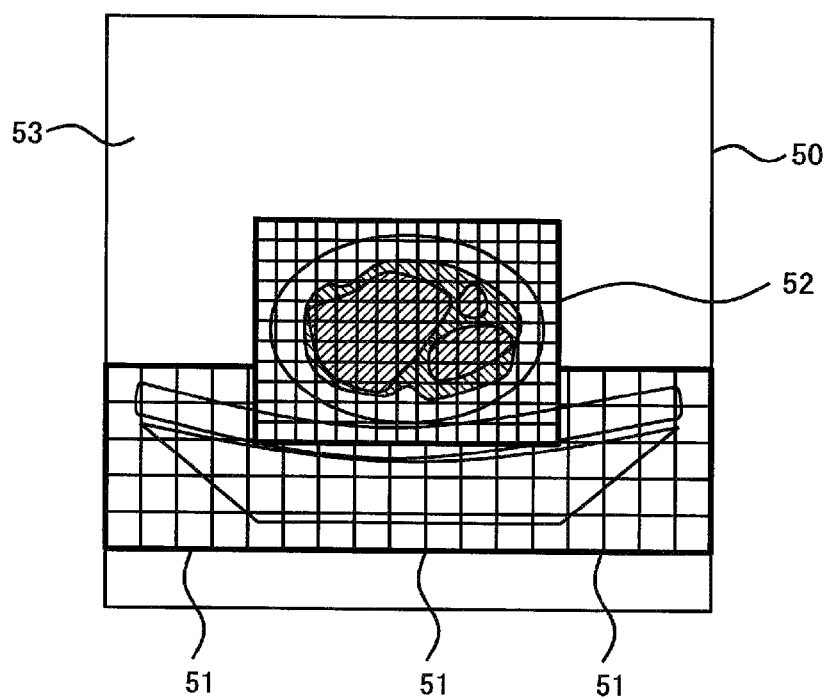

FIG. 7
(a)
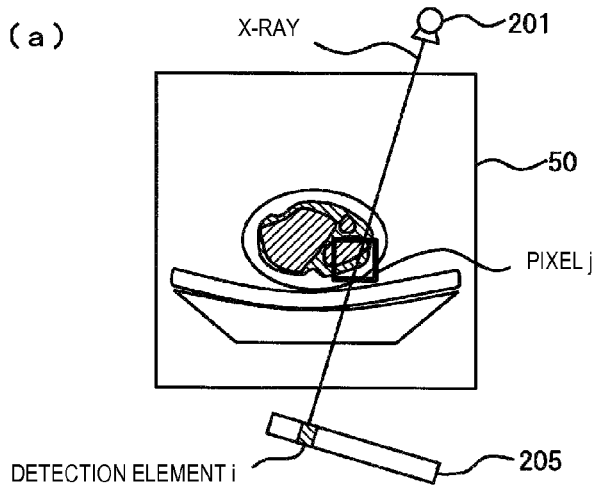
(b)
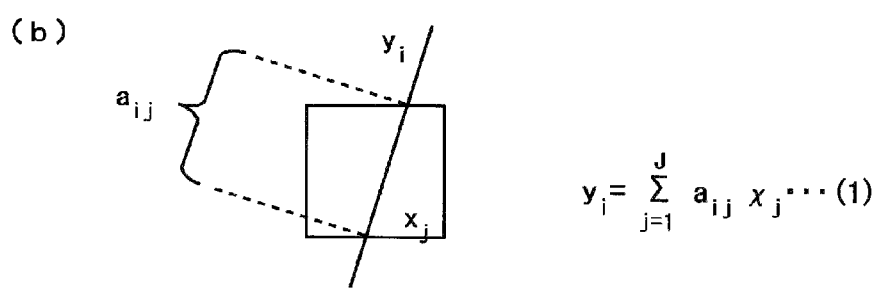
$$y_i = \sum_{j=1}^{J} a_{ij} x_j \cdots (1)$$
(c)
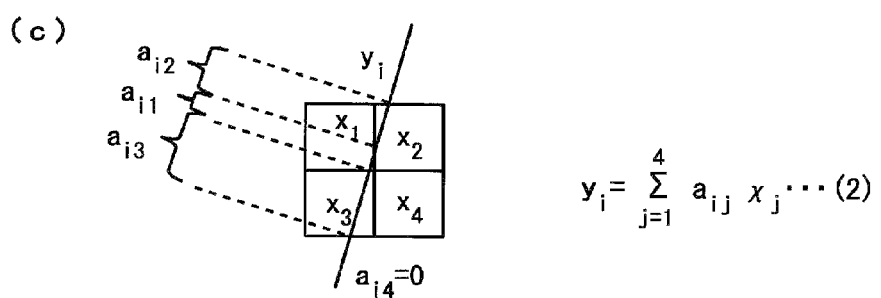
$$y_i = \sum_{j=1}^{4} a_{ij} x_j \cdots (2)$$
(3) IS SET, AND THE SUM OF TRANSMISSION LENGTHS IS DEFINED AS $a_{i1} + a_{i2} + a_{i3} + a_{i4} = a'_i \cdots (4)$
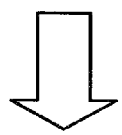
(d)
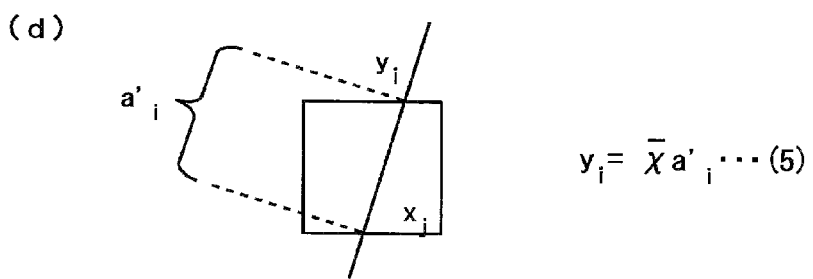
$$y_i = \bar{\chi} a'_i \cdots (5)$$

F I G . 1 0
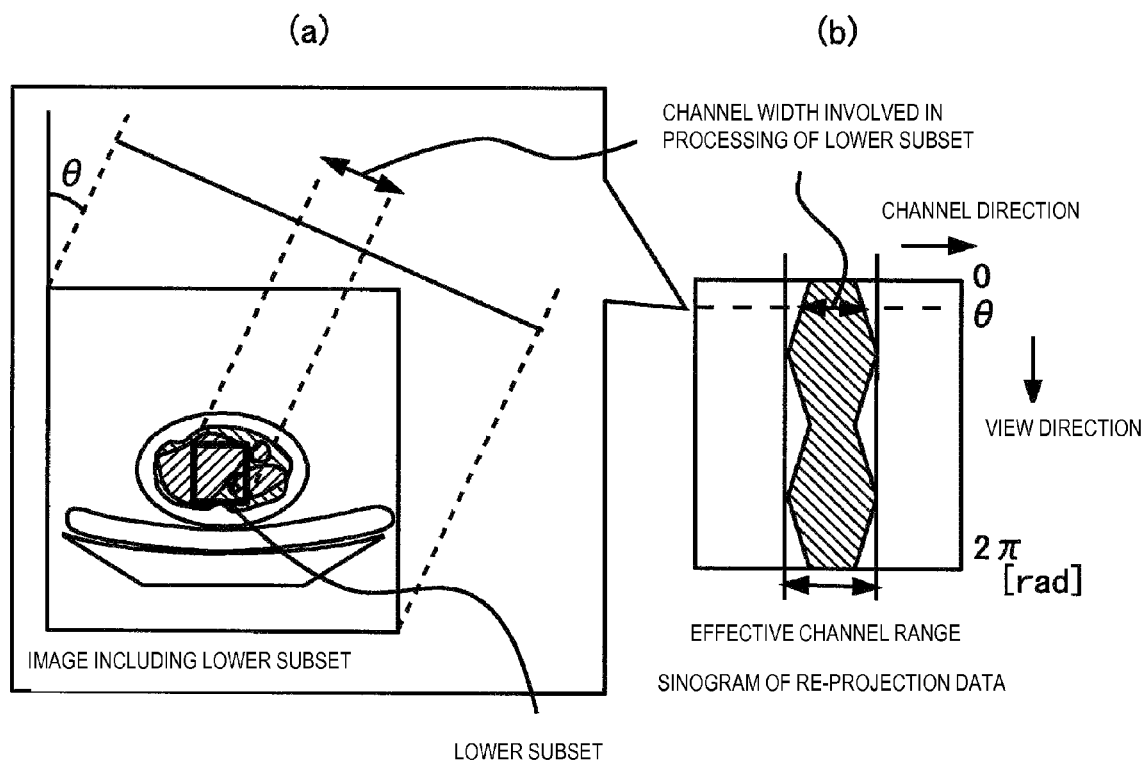

FIG. 14
(a) FAN BEAMS
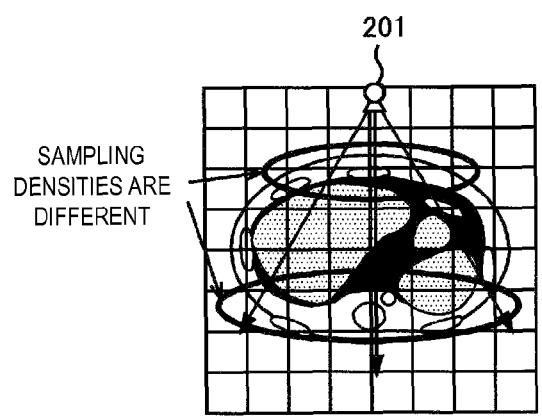
(b) PARALLEL BEAMS
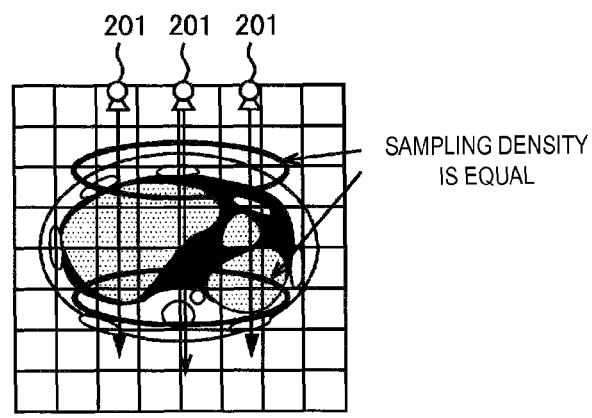

RECONSTRUCTION COMPUTING DEVICE, RECONSTRUCTION COMPUTING METHOD, AND X-RAY CT APPARATUS

TECHNICAL FIELD

The present invention relates to computation processing for reconstruction of an X-ray CT image using an iterative method.

BACKGROUND ART

An X-ray CT apparatus is an apparatus which emits X-rays from the periphery of an object, collects data regarding the intensity of X-rays transmitted through the object using an X-ray detector, and forms distribution information of an X-ray absorption coefficient inside the object as an image on the basis of the collected data.

The image reconstruction method is roughly divided into an analytical reconstruction method and an algebraic reconstruction method. Examples of the analytical reconstruction method of the image reconstruction method include a Fourier transform method, a filtered back projection method, and a convolution integral method, and examples of the algebraic reconstruction method include an iterative reconstruction method represented by an MLEM (Maximum Likelihood Expectation Maximization) method or an OSEM (Ordered Subset Expectation Maximization) method. Among these, when the analytical method that is currently commercialized is applied to a multi-slice CT with a wide cone angle (angle of an X-ray beam spreading in a slice direction), there is a problem in that cone beam artifacts are generated due to imperfections in the reconstruction algorithm. On the other hand, the algebraic reconstruction method is known to have high perfection compared with the analytical reconstruction method, while the computation time is long since the operation is performed recursively. For this reason, the algebraic reconstruction method has conventionally been used in the field of nuclear medical imagery, but is not popular in the field of X-ray CT imagery. However, the problem of the computation time in the algebraic reconstruction method (iterative reconstruction method) is being solved by the development of computer technology in recent years. PTL 1 discloses using an iterative reconstruction method for image formation of an X-ray CT apparatus to improve the image quality.

PTL 1 discloses a technique of suppressing the amount of computation while improving the image quality of a region of interest by setting the matrix size of the region of interest to be different from the matrix sizes of other regions and reconstructing an image using an iterative method.

In addition, PTL 2 discloses a technique of suppressing degradation of image quality in a region of interest, which is caused by degradation of image quality outside the region of interest, by sampling the region densely when a region where high resolution is required is present outside the region of interest.

In addition, PTL 2 discloses a technique of suppressing the amount of computation by increasing the convergence in the iterative method by estimating the convergence for each pixel and updating pixels selectively, which are to be updated, in an image.

CITATION LIST

Patent Literature

[PTL 1] U.S. Pat. No. 6,768,782
[PTL 2] US Patent Application Publication No. 2009/0190814

SUMMARY OF INVENTION

Technical Problem

In the above-described techniques disclosed in PTL 1 and PTL 2, the pixel size is set focusing on the required calculation accuracy and the iterative reconstruction is applied to an image configured to have a plurality of pixel sizes. In forward projection processing and back projection processing of the iterative reconstruction, however, an image with different pixel sizes between adjacent pixels requires time for processing, such as a scan of pixels, compared with an image with a uniform pixel size. In addition, a memory region for holding the matrix size for each pixel is needed. For this reason, when the iterative reconstruction is simply applied to an image with different pixel sizes, there has been a problem in that the amount of computation cannot be reduced effectively.

In addition, in the technique disclosed in PTL 2, it is necessary to calculate the degree of convergence of each pixel frequently. For this reason, there has been a problem in that time and memory for processing are required in a CT image with a large number of pixels.

The present invention has been made in view of the above problem, and it is an object of the present invention to provide a reconstruction computing device, a reconstruction computing method, and an X-ray CT apparatus capable of improving the image quality while reducing the amount of computation when reconstructing an X-ray CT image using an iterative method.

Solution to Problem

In order to achieve the above-described object, a first invention is a reconstruction computing device including: dividing means configured to group pixels of an initial image, which is reconstructed on the basis of X-ray projection data obtained by scanning an object, into subsets; setting means configured to set reconstruction conditions including at least convergence conditions and a pixel size for each of the subsets divided by the dividing means; and reconstruction means configured to update estimation images by performing iterative reconstruction under the reconstruction conditions set by the setting means for each of the subsets divided by the dividing means, the reconstruction means fixing estimation images or forward projection data of a subset satisfying the convergence conditions until other subsets satisfy the convergence conditions.

A second invention is a reconstruction computing method including: a dividing step of grouping pixels of an initial image, which is reconstructed on the basis of X-ray projection data obtained by scanning an object, into subsets; a setting step of setting reconstruction conditions including at least convergence conditions and a pixel size for each of the divided subsets; and a reconstruction step of updating estimation images by performing iterative reconstruction under the reconstruction conditions set in the setting step for each of the subsets, in which estimation images or forward projection data of a subset satisfying the convergence conditions is fixed until other subsets satisfy the convergence conditions.

A third invention is an X-ray CT apparatus including: a scanner which emits X-rays to an object from a plurality of angle directions around the object and collects X-ray projection data transmitted through the object; and a reconstruction computing device which reconstructs an X-ray CT image on the basis of the X-ray projection data collected by the scanner. The reconstruction computing device includes: dividing means configured to group pixels of an initial image, which is reconstructed on the basis of the X-ray projection data, into subsets; setting means configured to set reconstruction conditions including at least convergence conditions and a pixel size for each of the subsets divided by the dividing means; and reconstruction means configured to update estimation images by performing iterative reconstruction under the reconstruction conditions set by the setting means for each of the subsets divided by the dividing means, the reconstruction means fixing estimation images or forward projection data of a subset satisfying the convergence conditions until other subsets satisfy the convergence conditions.

Advantageous Effects of Invention

According to the present invention, it is possible to provide a reconstruction computing device, a reconstruction computing method, and an X-ray CT apparatus capable of improving the image quality while reducing the amount of computation when reconstructing an X-ray CT image using an iterative method.

BRIEF DESCRIPTION OF DRAWINGS

FIG. 1 is an external view showing the overall configuration of an X-ray CT apparatus 1.

FIG. 2 is a hardware block diagram of the X-ray CT apparatus 1.

FIG. 3 is a flow chart illustrating the flow of the entire process in the present invention.

[FIG. 4] FIG. 4(a) is a view showing an initial image 50, FIG. 4(b) is a view showing a subset of a bed region 51, and FIG. 4(c) is a view showing a subset of the object region 52.

[FIG. 5] FIG. 5 is a display example showing each subset on the initial image 50.

[FIG. 6] FIG. 6 is a view showing the pixel size set for each subset.

[FIG. 7] FIG. 7 is a view illustrating the relationship between the CT value and the projection value when pixels are combined.

FIG. 8 is a view illustrating the flow of an iterative process for an image divided into subsets with different pixel sizes.

FIG. 9 is a view illustrating the flow of an iterative process for an image divided into lower subsets.

[FIG. 10] FIG. 10 is a view illustrating a channel (effective channel range) involved at the time of forward projection of a lower subset.

FIG. 11 is a view illustrating a channel range held as forward projection data.

FIG. 12 is a view illustrating an example in which the reconstruction conditions are set for each region and an iterative process is performed under different convergence conditions in respective regions (image data update type).

FIG. 13 is a view illustrating an example in which the reconstruction conditions are set for each region and an iterative process is performed under different convergence conditions in respective regions (projection data update type).

[FIG. 14] FIG. 14 is a view illustrating the conversion of fan beam projection data into parallel beam projection data.

DESCRIPTION OF EMBODIMENTS

Hereinafter, preferred embodiments of the present invention will be described in detail with reference to the accompanying drawings.

In addition, in each of the following embodiments, an X-ray CT apparatus 1 may use a rotate-rotate method in which an X-ray source and an X-ray detector rotate together while emitting wide fan beams that cover the entire object, a scanning electron beam method of making electron beams hit a target electrode while deflecting the electron beams electrically, and the like, and the present invention may be applied to X-ray CT apparatuses based on any method.

[First Embodiment]

First, the configuration of the X-ray CT apparatus 1 of a first embodiment of the present invention will be described with reference to FIGS. 1 and 2.

Figure 1:
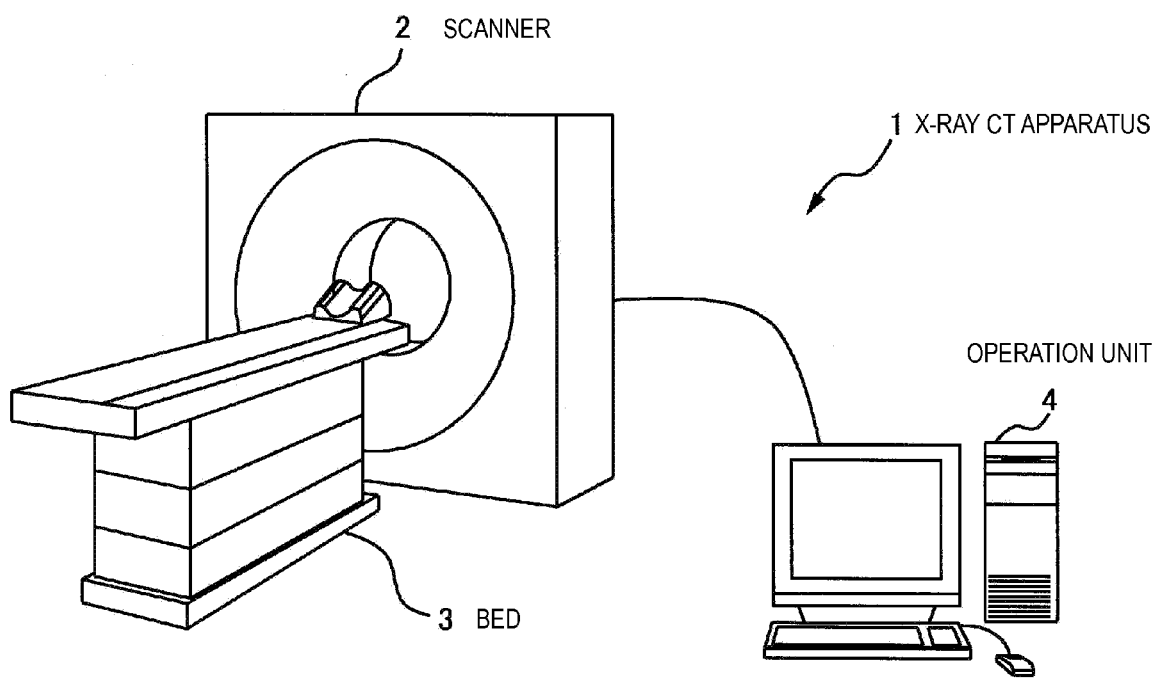
[FIG. 1]
Figure 2:
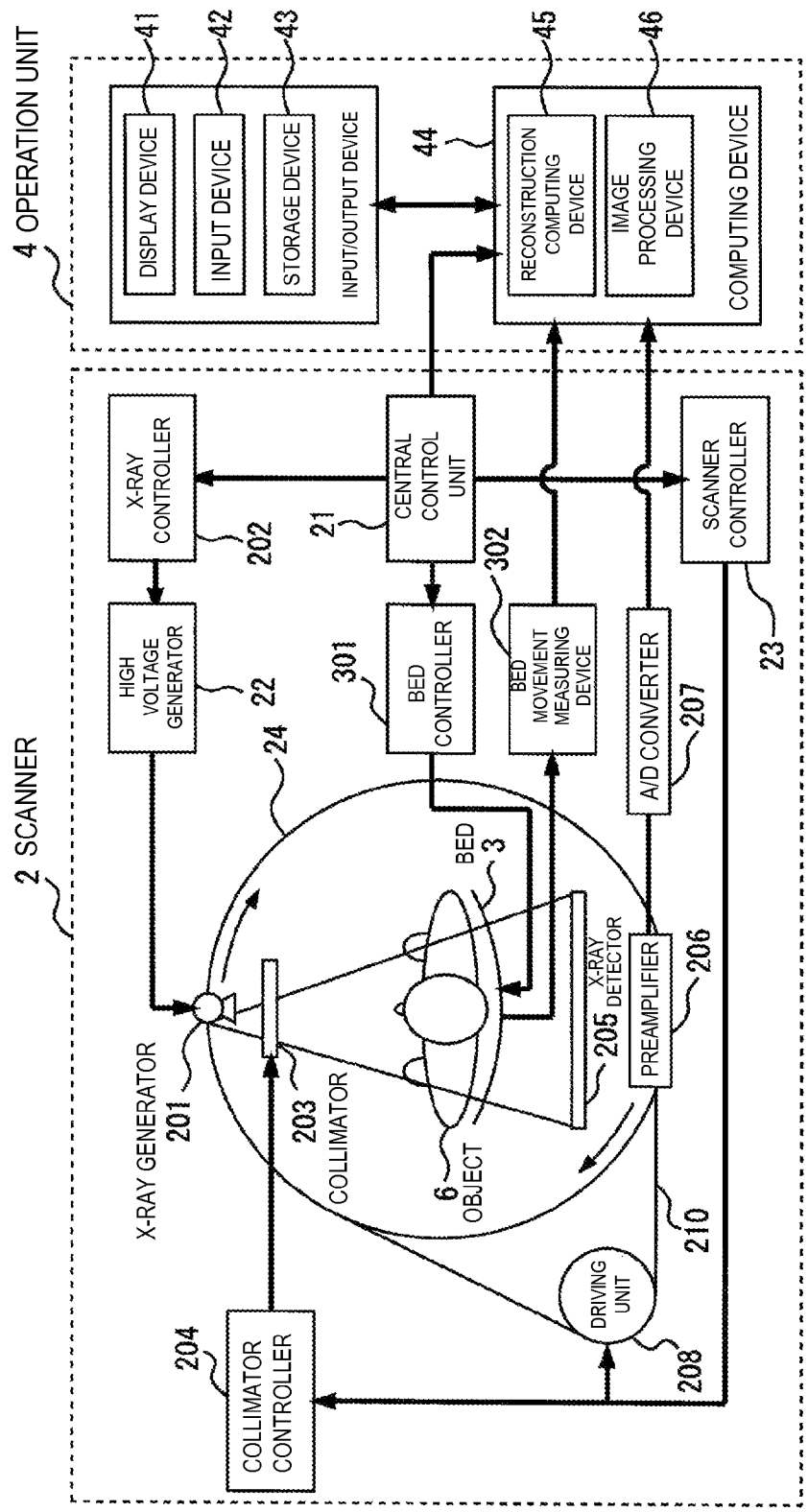
[FIG. 2]

As shown in FIGS. 1 and 2, the X-ray CT apparatus 1 is configured to include a scanner 2, a bed 3, and an operation unit 4. The X-ray CT apparatus 1 acquires projection data from each angle (view) around an object by carrying an object 6 fixed on the bed 3 into an opening of the scanner 2 and scanning the object 6.

As shown in FIG. 2, the scanner 2 is configured to include an X-ray generator (X-ray source) 201, a high voltage generator 22, an X-ray controller 202, a collimator 203, a collimator controller 204, an X-ray detector 205, a preamplifier 206, an A/D converter 207, a rotating plate 24, a driving unit 208, a driving transmission system 210, a scanner controller 23, and central control unit 21.

The X-ray generator 201 is an X-ray source and emits continuously or intermittently X-rays of intensity according to a tube voltage and a tube current, which are applied and supplied from the high voltage generator 22, to the object 6. The X-ray controller 202 controls the high voltage generator 22 according to a tube voltage and a tube current determined by the central control unit 21.

The collimator 203 forms X-rays emitted from the X-ray generator 201, for example, in the shape of cone beams (conical or pyramid-shaped beams) and emits the cone beams to the object 6, and is controlled by the collimator controller 204. X-rays transmitted through the object 6 are incident on the X-ray detector 205.

The X-ray detector 205 is formed by arraying, for example, about 1000 X-ray detection element groups, each of which is formed by the combination of a scintillator and a photodiode, in a channel direction (orbiting direction) and, for example, about 1 to 320 X-ray detection element groups in a column direction (body axis direction), and is disposed so as to face the X-ray generator 201 with the object 6 interposed therebetween. The X-ray detector 205 detects X-rays emitted from the X-ray generator 201 and transmitted through the object 6, and the detected X-ray projection data is amplified by the preamplifier 206. Then, the amplified X-ray projection data is output to the A/D converter 207.

The A/D converter 207 collects the X-ray projection data which has been detected by each X-ray detection element of the X-ray detector 205 and amplified by the preamplifier 206, converts the collected X-ray projection data into digital data, and output the digital data to a computing device 44 of the operation unit 4.

The X-ray generator 201, the collimator 203, the X-ray detector 205, the preamplifier 206, and the like are mounted on the rotating plate 24. The rotating plate 24 rotates with the driving force transmitted from the driving unit 208, which is controlled by the scanner controller 23, through the driving transmission system 210.

The central control unit 21 is configured to include a CPU (Central Processing Unit), a ROM (Read Only Memory), a RAM (Random Access Memory), and the like. The central control unit 21 controls the X-ray controller 202, the collimator controller 204, the scanner controller 23, and the computing device 44 of the operation unit 4, and also controls a bed controller 301 in the bed 3.

The bed 3 shown in FIGS. 1 and 2 is controlled by the bed controller 301, and is moved to predetermined height position, body axis position, and body width position. In this manner, the object 6 is carried into and taken out from the X-ray emission space of the scanner 2.

The operation unit 4 is configured to include a display device 41, an input device 42, a storage device 43, and the computing device 44. In addition, the computing device 44 includes a reconstruction computing device 45 and an image processing device 46. The operation unit 4 is connected to the scanner 2. Each section of the display device 41, the input device 42, the storage device 43, and the computing device 44 is controlled by the central control unit 21 in the scanner 2.

The display device 41 is formed by a liquid crystal panel, a display device such as a CRT monitor, and a logic circuit which cooperates with the display device to perform display processing, and is connected to the computing device 44. The display device 41 displays a reconstruction image (X-ray CT image), which is output from the computing device 44 by the central control unit 21 and the computing device 44, and various kinds of information handled by the central control unit 21.

The input device 42 is configured to include an input device, such as a keyboard, a mouse, and a ten key, and various switch buttons, for example, and outputs to the computing device 44 various kinds of instructions or information input by the operator. The computing device 44 outputs to the central control unit 21 the various kinds of instructions or information input from the input device 42. The operator operates the X-ray CT apparatus 1 interactively using the display device 41 and the input device 42.

The storage device 43 is formed by a hard disk or the like, and is connected to the computing device 44. The storage device 43 stores images output from the computing device 44 or programs and various kinds of data required for processing which will be described later.

The computing device 44 is formed by a CPU, a ROM, a RAM, and the like, and controls the entire operation unit 4 according to the control of the central control unit 21.

By control of the central control unit 21, the reconstruction computing device 45 acquires the X-ray projection data output from the A/D converter 207 in the scanner 2 and performs image reconstruction processing. That is, the reconstruction computing device 45 reconstructs an X-ray CT image of the object 6 by performing pre-processing, such as log conversion and calibration, for the acquired X-ray projection data and performing further processing to be described later (refer to FIG. 3) on the X-ray projection data. The reconstructed X-ray CT image is stored in the storage device 43 and is also displayed on the display device 41. The image processing device 46 is a device which performs image processing that the operator wants on the X-ray CT image generated by the reconstruction computing device 45.

Hereinafter, the operation of the X-ray CT apparatus 1 of the first embodiment will be described with reference to FIGS. 3 to 8.

The reconstruction computing device 45 of the X-ray CT apparatus 1 of the present invention generates an initial image reconstructed using an analytical method such as a filtered back projection method, divides pixels of the initial image according to the estimated required resolution, convergence, and the amount of features of the figure built on an image by subsets or according to one of these when grouping the pixels of the initial image into subsets, gives to each subset the reconstruction conditions including at least the convergence conditions, pixel size, and the number of subsets, performs an iterative process for each subset, and unites reconstruction images of the obtained subsets.

Here, the required resolution is the resolution of an image required to achieve the desired image quality. If the pixel size (length of one side of a pixel) is set to be small, the resolution is improved.

In addition, the convergence indicates a speed required until the pixel value converges through sequential update or the convergence conditions are satisfied. A pixel with higher convergence has a smaller number of repetitions required for update. In addition, the amount of features of the figure built on an image by a subset is the amount of features regarding the shape of a region corresponding to pixels in a subset, and indicates the complexity or Feret diameter, for example. Using these amounts of features as indices, a region corresponding to pixels in a subset is formed as a simple figure.

In the first embodiment, pixels of an initial image are divided into subsets corresponding to a bed region, an object region, and other regions (air region). This is because the required resolution and the convergence can easily be estimated before scanning in the bed region and other regions among these regions.

Figure 3:
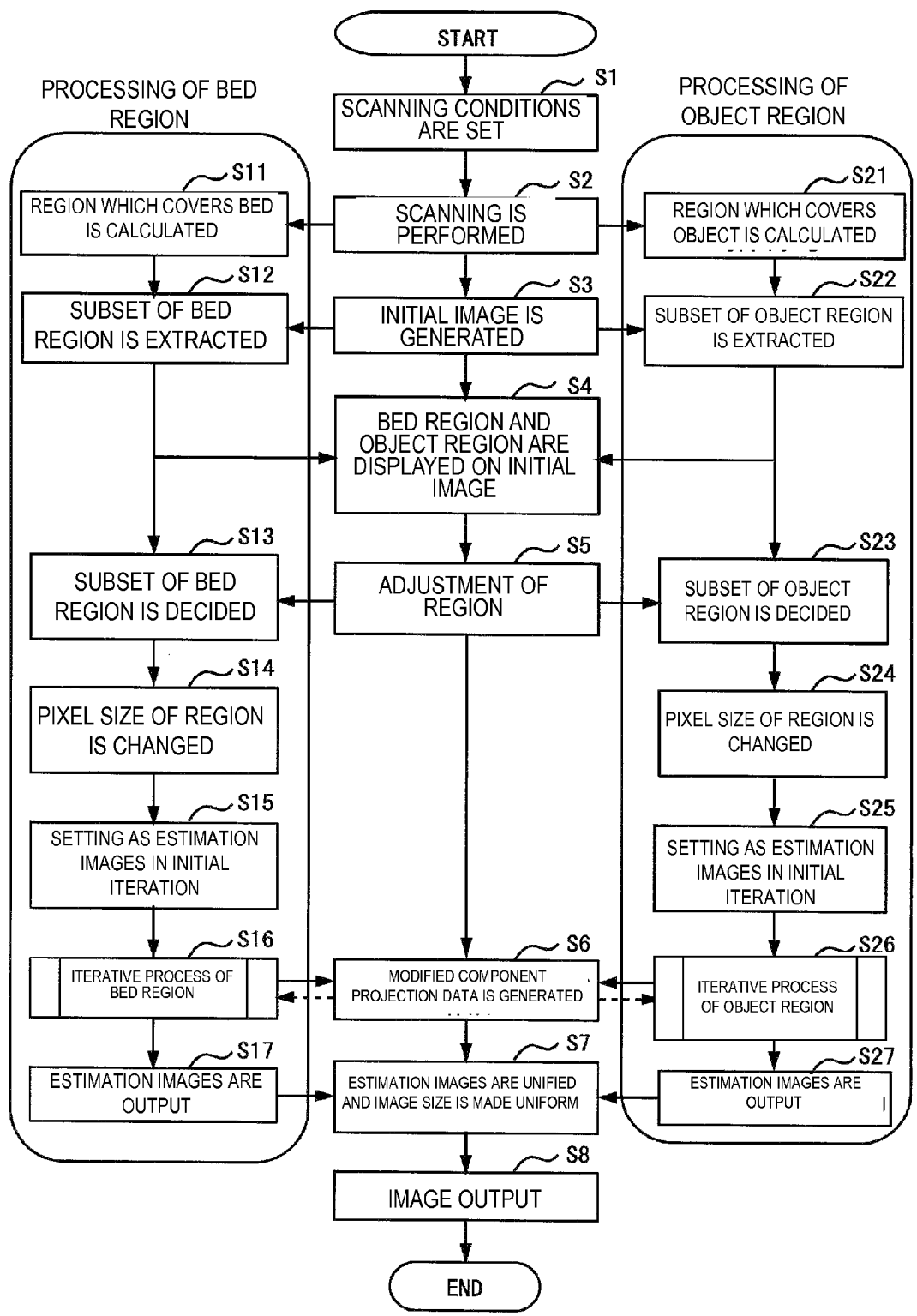
[FIG. 3]

When performing scanning and image reconstruction of the object 6, the central control unit 21 of the X-ray CT apparatus 1 of the present embodiment performs processing in the procedure of the flow chart shown in FIG. 3. That is, the central control unit 21 reads a program and data regarding the processing from the storage device 43 and performs processing in the following procedures on the basis of this program and data.

In advance of processing of step S1 in FIG. 3, it is assumed that scanogram imaging is performed in the X-ray CT apparatus 1 to generate a cross section model of an object based on the scanogram. In addition, it is assumed that the bed size, the bed position, and the like are acquired in advance.

The cross section model of an object is a model when the cross section of the object is assumed to be an ellipse, and is used for estimation of the object size and the like which will be described later. JP-A-2001-043993 discloses a method of estimating the object size.

The central control unit 21 receives a setting of scanning conditions and reconstruction conditions on the basis of the scanogram and the cross section model of an object. As the scanning conditions, for example, a bed moving speed, a tube current, a tube voltage, collimator conditions, a spiral pitch, a slice position, and the like may be mentioned. In addition, as the reconstruction conditions, reconstruction FOV, a reconstruction center position, a reconstruction pitch (slice thickness), a region of interest, a reconstruction image matrix size, a reconstruction filter function, the maximum number of repetitions of the iterative process, convergence conditions, and the like may be mentioned additionally (step S1).

Then, the central control unit 21 transmits a control signal required for scanning to the X-ray controller 202, the bed controller 301, and the scanner controller 23 on the basis of the scanning conditions input in step S1. The central control unit 21 transmits a scanning start signal to start scanning (step S2).

When the scanning is started, a control signal is transmitted from the X-ray controller 202 to the high voltage generator 22, so that a high voltage is applied to the X-ray generator 201. The X-ray generator 201 emits X-rays to the object 6. In this case, a control signal is transmitted from the scanner controller 23 to the driving unit 208, so that the X-ray generator 201, the X-ray detector 205, the preamplifier 206, and the like rotate around the object 6. On the other hand, the bed 3 on which the object 6 is carried by the bed controller 301 stops at a predetermined slice position at the time of a normal scan and is moved in parallel to the body axis direction at a predetermined spiral pitch at the time of a spiral scan.

X-rays emitted from the X-ray generator 201 are absorbed (attenuated) by each tissue in the object 6 after the emission region is restricted by the collimator 203, and the X-rays are transmitted through the object 6 to be detected by the X-ray detector 205. The X-rays detected by the X-ray detector 205 are converted into a current, is amplified by the preamplifier 206, are converted into digital data by the A/D converter 207, and is output to the computing device 44 of the operation unit 4. The computing device 44 performs log conversion or calibration for the acquired digital data, thereby obtaining projection data. This projection data is subjected to reconstruction computation of the reconstruction computing device 45.

When the projection data is acquired, the reconstruction computing device 45 generates an initial image 50 first (step S3).

That is, the reconstruction computing device 45 reconstructs the initial image 50 on the basis of the projection data using an analytical reconstruction method, such as the Feldkamp method. The entire initial image 50 is formed in a uniform pixel size. An example of the initial image 50 is shown in FIG. 4(a). As shown in FIG. 4(a), the reconstruction FOV of the initial image 50 is assumed to be the entire scanning range. This is to make inconsistency between actual projection data and forward projection data of estimation images as small as possible in an iterative process performed later.

In addition, as an analytical reconstruction method for obtaining the initial image 50, it is possible to use any of the Radon transformation method, the Fourier transform method, and the filtered back projection method (FBP method). However, in the case of a multi-slice CT apparatus with the X-ray detector 205 of about 64 columns, for example, filtered 3D back projection processing based on the Weighted Feldkamp method or its improved processing is appropriate. When the filtered 3D back projection processing based on the Weighted Feldkamp method is adopted, reconstruction processing is performed in consideration of the cone angle. Accordingly, since the number of repetitions until the convergence of the iterative process performed later is reduced, the computation time can be shortened.

Then, the reconstruction computing device 45 calculates a region, which covers the bed of the initial image 50, on the basis of the bed position set when performing scanning and the bed size calculated in advance. Hereafter, the region which covers the bed is called a bed region 51. As shown in FIG. 4(b), the bed region 51 may be a rectangular shape, and the amount of bending of the table by the weight of the object may be added to the horizontal and vertical sides when necessary (step S11). Here, since the case where pixels are aligned on the lattice points is described, the bed region 51 has a rectangular shape. However, it is possible to set the region in a different shape depending on the configuration of pixels. For example, when the Polar voxel is a base of an image, the region may be set in a fan shape.

In addition, on the basis of the calculated bed region information, the reconstruction computing device 45 extracts pixels included in the bed region 51 from the initial image 50 and groups the pixels into a subset. In addition, a layer having this entire subset as one image plane is built (step S12). The layer of the subset of the bed region 51 is called a first layer herein.

In addition, the reconstruction computing device 45 calculates the object size from the scanogram obtained when setting the scanning conditions or the cross section model of the object generated on the basis of the scanogram, and calculates a region which covers the object 6 using the bed position set when performing scanning. Hereinafter, the region which covers this object 6 is called an object region 52. As shown in FIG. 4(c), the object region 52 may be a rectangular shape, and it is possible to set the margin so that the clothing of the object 6 does not protrude and to add the margin to each of the rectangular horizontal and vertical sides (step S21). In addition, although the object region 52 is a rectangular shape, it is possible to set the region in a different shape depending on the configuration of pixels for the same reason as in the case of the bed region 51.

On the basis of the calculated object region information, the reconstruction computing device 45 extracts pixels included in the object region 52 from the initial image 50 and groups the pixels into a subset. In addition, a layer having this entire subset as one image plane is built (step S22). The layer of the object region 52 is called a second layer herein.

Then, the reconstruction computing device 45 displays the initial image 50 generated in step S3 on the display device 41. In addition, as shown in FIG. 5(a), the bed region 51 and the object region 52 extracted in step S12 and step S22 are displayed on the initial image 50 (step S4).

In this step, the operator may reset the bed region 51 and the object region 52. After the region resetting of the operator through the input device 42, the central control unit 21 transmits the reset bed region 51 and the reset object region 52 to the reconstruction computing device 45, and the reconstruction computing device 45 adjusts each subset (first and second layers) of the bed region 51 and the object region 52 with the reset content (steps S13 and S23).

In addition, for the bed region 51, the reconstruction computing device 45 performs up-sampling or down-sampling of pixels included in the bed region 51 according to the required resolution of the bed 3 (step S14). It is assumed that the required resolution of the bed 3 is calculated in advance from the image quality to be obtained.

Similar for the object region 52, the reconstruction computing device 45 performs up-sampling or down-sampling of pixels included in the object region 52 (step S24). It is assumed that the pixel size of the object region 52 is determined on the basis of the reconstruction conditions set in step S1.

At this point in time, pixels included in both the object region 52 and the bed region 51 are present. On the basis of the result of the above-described pixel size setting processing, these pixels are added to a subset preferentially for a region with a smaller pixel size. As a result, when the shape of the region is no longer a rectangle, the region is subdivided to maintain a rectangle as shown in FIG. 5(b).

An image (first layer) of the bed region 51 whose pixel size has been changed by the pixel combination is set as a estimation image (refer to 56 in FIG. 8) in the first iteration in the iterative process (step S15). In addition, the reconstruction computing device 45 sets an image (second layer) of the object region 52 whose pixel size has been changed as a estimation image (refer to 57 in FIG. 8) in the first iteration in the iterative process (step S25).

By the processing up to here, the initial image 50 is divided into three regions of the bed region 51, the object region 52, and the other region 53. The other region 53 is called the air region 53 hereinafter.

As shown in FIGS. 6(a) and 6(b), the pixel size corresponding to the required resolution is set for each of the regions 51, 52, and 53. Since higher resolution is generally required for the object region 52, the pixel size of the object region 52 is set to the minimum size. In addition, since less attention is paid to the air region 53 in medical diagnosis, it is assumed that an iterative process is not performed and the CT value of the air calculated in advance is given to the air region 53. In addition, the pixel size is set as large as possible.

The pixel size of the bed region 51 is set to an appropriate size according to the required image quality and calculation speed.

FIG. 7 shows the relationship between the CT value and the projection value when pixels are combined.

As shown in FIGS. 7(*a*) and 7(*b*), the projection value and the CT value after log conversion in a pixel j of the initial image 50 are set to $y_i$ and $x_j$, respectively, and the transmission length in the pixel j of an X-ray incident on a detection element i is $a_{ij}$.

In this case, the following Expression (1) is satisfied.

[Expression 1]

$$y_i = \sum_{j=1}^{J} a_{ij} x_j \quad (1)$$

As shown in FIG. 7(*c*), for example, when four pixels of j=1, 2, 3, and 4 are combined, the projection value $y_i$ is expressed by the following Expression (2).

[Expression 2]

$$y_i = \sum_{j=1}^{4} a_{ij} x_j \quad (2)$$

In each embodiment of the present invention, when combining pixels, pixels with small CT value differences between an observed pixel and adjacent pixels are combined. Therefore, Expression (3) is assumed.

[Expression 3]

$$x_1 \approx x_2 \approx x_3 \approx x_4 \cong \bar{x} \quad (3)$$

In addition, Expression (4) defines the sum of transmission lengths in respective pixels (j=1, 2, 3, and 4) of X-rays incident on the detection element i.

[Expression 4]

$$a_{i1} + a_{i2} + a_{i3} + a_{i4} = a'_i \quad (4)$$

In this case, the relationship between the projection value and the CT value for the combined pixel is expressed by the following Expression (5).

[Expression 5]

$$y_i = \bar{x} a'_i \quad (5)$$

Explanation returns to FIG. 3.

When the appropriate pixel size is given to each subset (the bed region 51 and the object region 52) and the estimation image in the first iteration is given by the processing in steps S1 to S5, steps S11 to S15, and steps S21 to S25, the reconstruction computing device 45 starts an iterative process for each of the bed region 51 and the object region 52 (steps S16 and S26).

As the iterative process, it is preferable to use known methods, such as the ML (Maximum Likelihood) method, the MAP (Maximum a Posterior) method, the WLS (Weighted Least Squares) method, the PWLS (Penalized Weighted Least Squares) method, and the SIRT (Simultaneous Reconstruction Technique) method. In addition, it is also possible to apply a method for a speed increase, such as the OS (Ordered Subset), to the iterative process.

The flow of the iterative process will be described with reference to FIG. 8.

Figure 8:
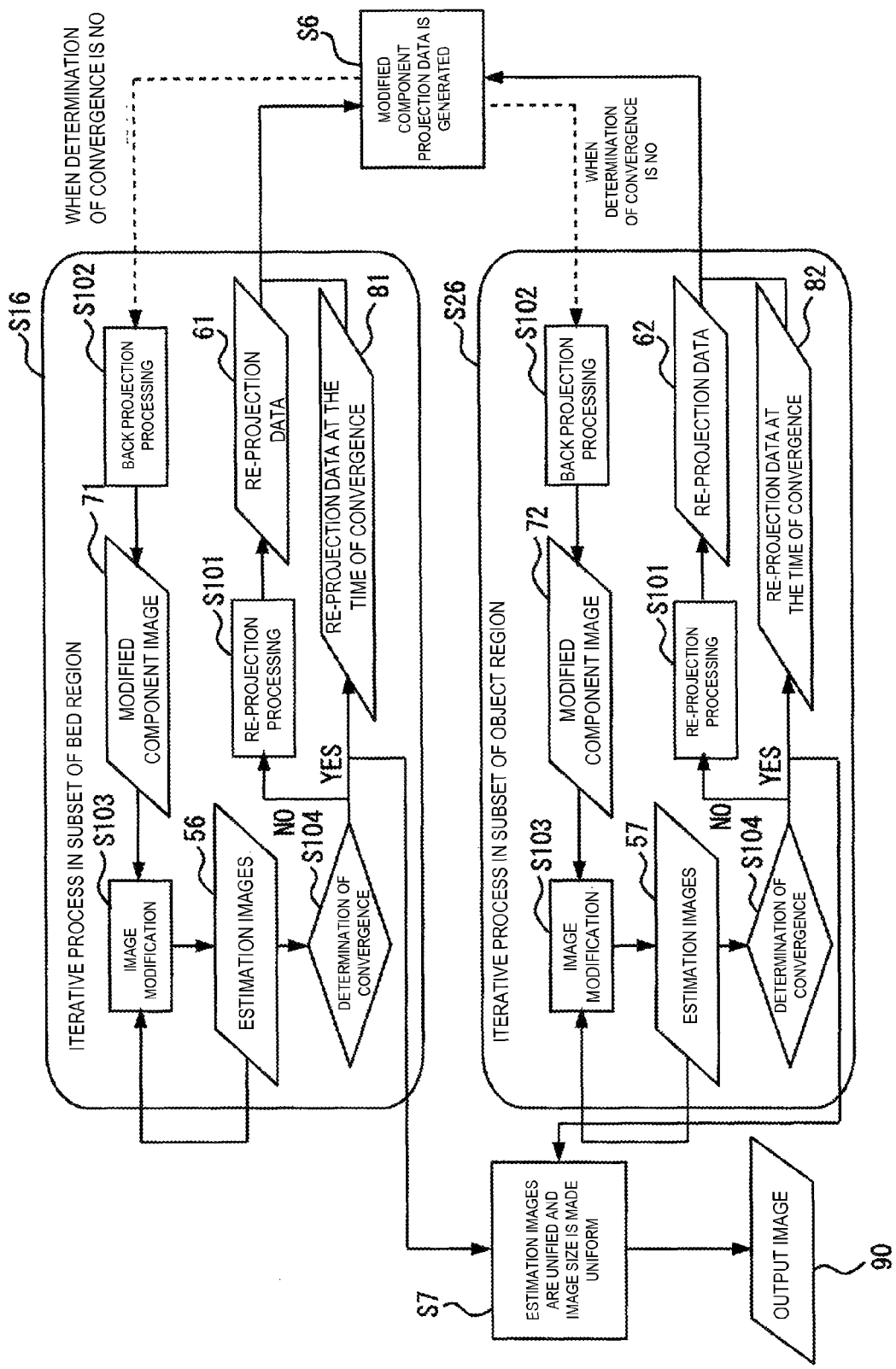
[FIG. 8]

In an iterative process (S16) in a subset of the bed region 51 shown in FIG. 8 and an iterative process (S26) in a subset of the object region 52, only estimation images used in the first iteration are different, and the procedure is the same.

That is, in the iterative process S16 for the bed region 51, the reconstruction computing device 45 performs forward projection processing of the estimation image of the bed region 51 (step S101) to obtain forward projection data 61. Similarly, in the iterative process S26 for the object region 52, the reconstruction computing device 45 performs forward projection processing of the estimation image of the object region 52 (step S101) to obtain forward projection data 62. Then, the reconstruction computing device 45 unifies the forward projection data 61 and 62 and compares the result with actual projection data to generate modified component projection data (step S6).

Using this modified component projection data, back projection is performed in the bed region 51 in the iterative process S16 for the bed region 51, and back projection is performed in the object region 52 in the iterative process S26 for the object region 52 (step S102). As a result, modified component images 71 and 72 of the bed region 51 and the object region 52 are acquired.

Then, using the modified component images 71 and 72, the estimation images 56 and 57 are modified (step S103) and updated. For each of the updated estimation images 56 and 57, it is determined whether or not the convergence conditions set in advance are satisfied (step S104). When the convergence conditions are not satisfied (step S104; No), the processing in steps S101 to S104 is repeated.

When the iteration is repeated as described above and the convergence conditions are satisfied for a certain region (subset) (step S104; Yes), subsequent iterations are not performed for the subset. In addition, for a subset which does not satisfy the convergence conditions, it is possible to reset the reconstruction conditions, such as the number of subsets, the convergence conditions, and the pixel size. In step S6, when one of subsets converges, forward projection data 81 (or 82) of the convergent subset is fixed, and the fixed forward projection data 81 and forward projection data 62 (or 61) under iteration are unified to generate modified component projection data. By this processing, the convergence difference for each subset can be reduced. As a result, it is possible to reduce the amount of computation. In addition, the convergence can be optimized by changing the reconstruction conditions according to the convergence situation of other subsets.

When the convergence conditions are satisfied for all subsets, the iteration is ended, estimation images at the time of convergence of each subset is output, and the process proceeds to step S7 (step S104 in FIG. 8 "Yes"->step S7 (steps S17 and S27 in FIG. 3->step S7)).

In step S7 (FIGS. 3 and 8), the estimation image at the time of convergence for the bed region 51 and the estimation image at the time of convergence for the object region 52 are unified. The pixel size of each layer of the bed region 51, the object region 52, and the air region 53 is made uniform by up-sampling or down-sampling, and the result is output as an output image 90 (step S8; FIG. 3).

A known CT value equivalent to the air is given to each pixel in the air region 53.

By the above processing, the output image 90 of the present embodiment is generated with high resolution in the object region 52, with approximately middle to high resolution in the bed region 51, and with approximately middle or lower resolution in the air region 53.

As described above, in the first embodiment, the reconstruction computing device 45 divides the initial image 50 into the bed region 51, the object region 52, and the other air region 53 as regions according to the required resolution using the Feldkamp method or the like, sets the reconstruction conditions for each of the divided regions, and performs an iterative process. In the iterative process, forward projection data of estimation images of the respective regions is generated and unified, the unified data is compared with actual projection data to estimate modified component projection data, back projection processing of each region is performed on the modified component projection data to generate a modified component image of each region and modify the estimation images. The above processing is repeated until the convergence conditions set for each region are satisfied. When the convergence conditions are satisfied for a certain subset, estimation images (or forward projection data) of the region are fixed and the above iteration is repeated for other subsets. In addition, when the convergence conditions are satisfied for all regions, estimation images of each region are unified, pixels are made uniform, and the result is output as the output image 90.

Therefore, it is possible to obtain the good image quality with improved resolution in a region where pixels are set densely. On the other hand, for a subset which does not require high resolution, such as a bed or air, the image quality can be ensured even if the pixel size is set coarsely. In this case, the computation time can be shortened by increasing the speed of convergence in the iterative process. In addition, when the iterative reconstruction is applied to an image with different pixel sizes, it takes time to perform a pixel scan or the like. However, it is possible to simplify the processing by setting the pixel size for each subset and accordingly, to increase the processing speed. In addition, when the convergence conditions are set for each pixel and the iterative reconstruction is applied, it is necessary to update the convergence conditions for all pixels and accordingly, a large amount of memory and computation time can be required. However, since the processing can be simplified by setting the convergence conditions for each subset, it is possible to reduce the required amount of memory and the required amount of computation.

[Second Embodiment]

Next, a second embodiment of the present invention will be described with reference to FIG. 9.

In addition, the hardware configuration of an X-ray CT apparatus 1 of the second embodiment is the same as that of the X-ray CT apparatus 1 of the first embodiment shown in FIGS. 1 and 2. Therefore, explanation thereof will be omitted, and the same reference numerals are given to the same sections for the following explanation.

As a reconstruction computing device 45 of the second embodiment, it is assumed that a multi-core processor dedicated to high-speed operation is used. Since a memory of each core is generally small in the multi-core processor, the number of pixels and the number of projection data which can be collectively processed are limited. In addition, in the iterative process, the ratio of processing of data transfer of each core to a memory is high. For this reason, the amount of data according to the throughput of each core is set as the amount of data which can be collectively processed in the core to reduce the number of times of data transfer, so that the iterative process can be performed efficiently.

That is, in the second embodiment, it is assumed that pixels included in a subset in the first embodiment is further grouped into lower subsets with a predetermined number of pixels and an iterative process (forward projection processing and back projection processing) is performed collectively for pixels in the lower subset.

The reconstruction computing device 45 sets lower subsets for the divided subsets so as to satisfy the following conditions (A) to (C).

(A) A lower subset should have the optimal number of pixels for the throughput (the amount of memory) of the reconstruction computing device 45.

(B) At least one pixel adjacent to each pixel in a lower subset should be included in the same group.

(C) A region on an image formed by all pixels included in a lower subset should have a shape similar to a region shown by a unit pixel.

When a region on an image formed by all pixels included in a lower subset protrudes from a region on an image formed by all pixels included in a subset, the reconstruction computing device 45 resets either the pixels included in the lower subset or the pixels included in the subset so that the above-described conditions (A), (B), and (C) are satisfied.

According to the above-described conditions, for example, the bed region 51 of the first embodiment is divided into four lower subsets 51a, 51b, 51c, and 51d, and the object region 52 is divided into four lower subsets 52a, 52b, 52c, and 52d.

Figure 9:
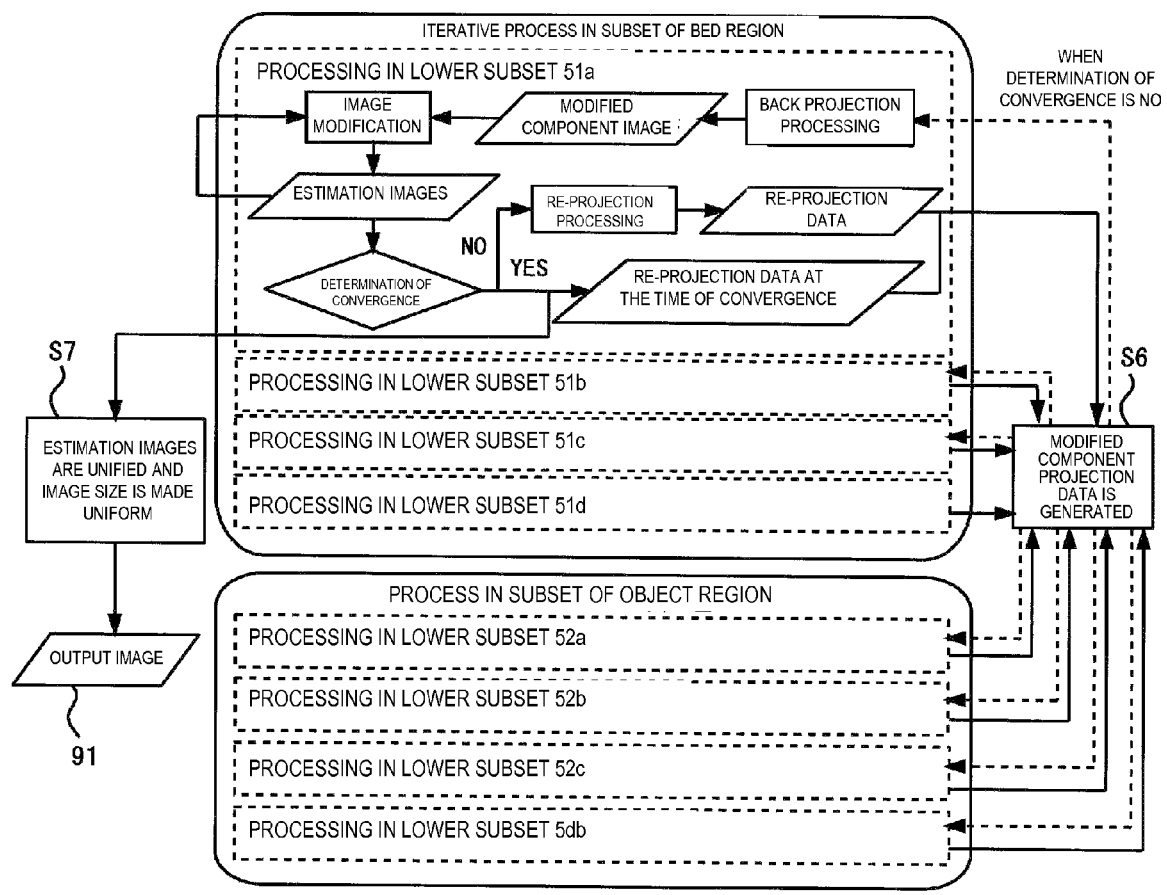
[FIG. 9]

FIG. 9 shows the flow of the iterative process for an image divided into lower subsets.

The reconstruction computing device 45 assigns the above-described eight lower subsets 51a, 51b, 51c, 51d, 52a, 52b, 52c, and 52d to respective core processors to perform an iterative process. For example, processing of the lower subset 51a is assigned to a core processor 45a, processing of the lower subset 51b is assigned to a core processor 45b, processing of the lower subset 51c is assigned to a core processor 45c, and the like, so that pixels in the lower subset are collectively processed by the assigned core processor.

The procedure of iterative reconstruction in each lower subset is the same as that in the first embodiment (steps S16 and S26 in FIG. 8). As shown in FIG. 9, the reconstruction computing device 45 unifies forward projection data of all of the lower subsets 51a, 51b, 51c, 51d, 52a, 52b, 52c, and 52d after forward projection processing and compares the unified forward projection data with actual projection data to generate modified component projection data. A modified component image is generated by performing back projection of the modified component projection data separately for each lower subset, and the modified component image is added to a estimation image in the previous iteration to update the estimation image. In a certain lower subset, forward projection is performed when the estimation image after updating does not satisfy the convergence conditions set in advance, and the iteration is repeated until the convergence conditions are satisfied. On the other hand, when a certain lower subset satisfies the convergence conditions, subsequent iterations are not performed, and the forward projection data at the time of convergence is provided and is unified with forward projection data of other lower subsets. When all lower subsets satisfy the convergence conditions, all iterations are ended, and an image with a uniform pixel size is output by up-sampling or down-sampling.

In addition, although an example where determination of the convergence conditions is performed for each lower subset is shown, it is also possible to set the convergence conditions for each subset or the entire image and to perform determination.

As described above, according to the second embodiment, a subset is further divided into lower subsets suitable for the amount of memory of each core processor and processing is performed for each subset. Therefore, since parallel processing using a multi-core processor in which the amount of memory of each core is small is possible, the iterative process can be performed efficiently.

[Third Embodiment]

Figure 11:
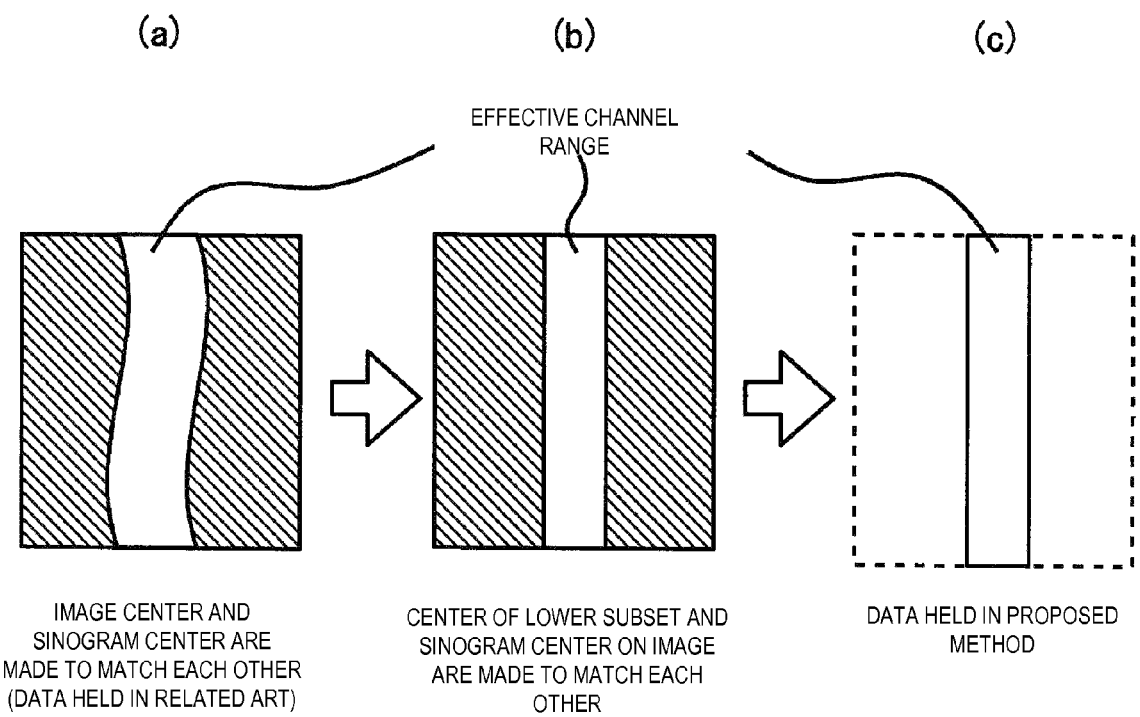
[FIG. 11]

Next, a third embodiment of the present invention will be described with reference to FIGS. 10 and 11.

In addition, the hardware configuration of an X-ray CT apparatus 1 of the third embodiment is the same as that of the X-ray CT apparatus 1 of the first embodiment shown in FIGS. 1 and 2. Therefore, explanation thereof will be omitted, and the same reference numerals are given to the same sections for the following explanation.

In the above second embodiment, an example is shown in which a subset is further divided into lower subsets, which are smaller processing units than the subset, and each core processor performs processing for each of the lower subsets. In the third embodiment, an example will be described in which an iterative process is performed efficiently by excluding a redundant portion of data held by each core processor.

Each divided lower subset is only a part of the initial image 50, and the number of channels involved in the operation is also a part of all channels.

As shown in FIG. 10(a), at the viewing angle θ, the channel width relevant to forward projection of a lower subset and the like is some channels of the entire detector. When this is viewed on a sinogram in FIG. 10(b), there is a variation in the channel direction for each view, but channels involved in forward projection or back projection of the lower subset are some of all channels in each view. Accordingly, each core processor does not need to hold the data of a channel which is not related to the lower subset to be processed.

In the third embodiment, therefore, the reconstruction computing device 45 calculates first a channel width involved in forward projection and back projection of a lower subset for each view. Hereinafter, as shown in FIG. 10(b), a channel involved in forward projection and back projection of a lower subset is called an involved channel, and a range obtained by extending an involved channel of each view to the width of an involved channel with the maximum width in all views is called an effective channel range. The effective channel range can be calculated from the position and the projection angle (viewing angle) of a lower subset on an image.

In addition, on the basis of the position on an initial image of an observed lower subset, the reconstruction computing device 45 calculates the amount of shift in the channel direction in each view of the effective channel range so that the center of the effective channel range in each view matches the center of all channels. Then, the reconstruction computing device 45 processes only the data of the effective channel range in the processing for each lower subset.

Specifically, when the observed lower subset is located at a different position from the center of the image, the effective channel range draws a sine curve in all views as shown in FIG. 11(a). In the related art, forward projection data is also stored for channels other than the channel involved in the observed lower subset. In the present embodiment, however, the center of the effective channel range is shifted in the channel direction so as to match the center of the sinogram (entire forward projection data) as shown in FIG. 11(b), and only the forward projection data of the effective channel range is held as shown in FIG. 11(c). The amount of data that is held is data equivalent to the number of channels in the effective channel range× the number of views.

The reconstruction computing device 45 also holds the amount of shift of the effective channel range in the channel direction in each view. The amount of shift in the channel direction may be the amount of movement in real space or may be an index of a channel.

At the time of back projection processing in the iterative process, the reconstruction computing device 45 shifts the held forward projection data of each lower subset to the original channel position with reference to the amount of shift described above and then generates forward projection data (or modified forward projection data) of the entire image. Then, the reconstruction computing device 45 obtains back projection data of the observed lower subset.

As described above, in the third embodiment, the reconstruction computing device 45 calculates an involved channel with a maximum width, among involved channels that are involved in a lower subset at the time of forward projection and back projection, as an effective channel range and calculates the amount of shift in the channel direction in each view in order to match the center of the effective channel range in each view to the center of all channels. In addition, when performing forward projection processing, the reconstruction computing device 45 holds data of the effective channel range of the observed lower subset. When performing back projection processing, the reconstruction computing device 45 shifts the held forward projection data of each lower subset to the original channel position on the basis of the amount of shift, thereby obtaining the back projection data of the observed lower subset.

Accordingly, when a subset is further divided into lower subsets to perform processing, it is not necessary to hold data unnecessary for the computation. As a result, it is possible to eliminate redundant data transfer.

[Fourth Embodiment]

Next, a fourth embodiment of the present invention will be described with reference to FIGS. 12 and 13.

In addition, the hardware configuration of an X-ray CT apparatus 1 of the fourth embodiment is the same as that of the X-ray CT apparatus 1 of the first embodiment shown in FIGS. 1 and 2. Therefore, explanation thereof will be omitted, and the same reference numerals are given to the same sections for the following explanation.

In the fourth embodiment, reconstruction processing will be described in which an operator designates an image region (image FOV) that the operator wants to generate finally inside the object region 52 divided in the first embodiment.

In the iterative reconstruction, if the FOV size of an image to be reconstructed is made small compared with the entire scanning range, inconsistency between the forward projection data and the actual projection data occurs. This degrades the image quality. For this reason, it is necessary to determine the FOV size or the reconstruction center position in the iterative reconstruction such that the entire object is included. In addition, if the FOV size is increased without changing the image matrix size (the number of pixels of one side of an image), a discrete error increases. Accordingly, in order to reconstruct a part of the object with high resolution, it is necessary to increase the image matrix size. However, if the image matrix size is increased N times, the number of pixels is increased $N^2$. As a result, the time taken for forward projection is increased N times and the time taken for back projection is increased $N^2$.

In the fourth embodiment, therefore, the reconstruction computing device 45 divides the entire scanning range region (ROI1) into an image region (ROI2), which needs to be generated finally, and the other region (ROI3) and also sets convergence conditions (CC2 and CC3) for the ROI2 and ROI3, respectively, and performs an iterative process over a plurality of divided stages.

In the first-stage iterative process, an error component (modified component) in each of the ROI2 and ROI3 is evaluated while the iterative process for ROI1 (ROI2+ROI3) is being performed. After the ROI3 satisfies the convergence conditions CC3, the process proceeds to the second-stage iterative process. In the second-stage iterative process, the ROI3 component is fixed, and the iterative process is performed for the ROI2 region on the basis of the convergence conditions CC2.

In addition, when performing the second-stage process (iterative process for the ROI2 region), the reconstruction conditions (the number of subsets, image matrix size, the number of reconstruction slices, a distance between reconstruction slices, a reconstruction center position, and the like) may changed, when necessary, such that an error in the ROI2 is reduced.

Specifically, the object 6 is photographed first on the basis of the scanning conditions input through the input device 42, as in steps S1 to S3 in the first embodiment. Then, when the reconstruction conditions, such as the reconstruction FOV, are set, the reconstruction computing device 45 generates a reconstruction image from the projection data obtained by scanning using the filtered back projection (FBP) method.

For example, as reconstruction conditions (RCND) in this stage, the reconstruction FOV (FOV2) or the reconstruction center position is determined such that the disease is easily diagnosed depending on a portion to be photographed (for example, in heart scanning, the reconstruction FOV (FOV2) is 250 mm and the reconstruction center position is set such that the heart becomes the center), the reconstruction image matrix size is normally fixed as 512 pixels (indicating the number of pixels of one side of the rectangle), the number of reconstruction image slices and the distance between slices are set according to the scanning range or the size of the disease to be diagnosed (for example, the number of slices is 200 and the distance between slices is 0.5 mm), and a filter having the frequency characteristics which make it easier to diagnose the disease depending on a portion to be diagnosed (for example, in the chest, a filter which emphasizes a high-frequency component of a lamp filter) is selected as a reconstruction filter.

The operator checks the image obtained in step S3. When noise or artifacts become a serious problem, the operator sets, through the input device 42, the maximum number of repetitions of the iterative process (the maximum number of repetitions N2 with respect to the FOV2 region and the maximum number of repetitions N1 with respect to the entire image (FOV1)), the number of subsets SUB1 with respect to the entire image (FOV1) and the number of subsets SUB2 with respect to the FOV2 region, and the convergence conditions CC2 with respect to the FOV2 region and the convergence conditions CC1 with respect to the entire image (FOV1) and selects a processing execution button (when the convergence conditions are satisfied within the maximum number of repetitions, the process is ended in a stage in which the convergence conditions are satisfied).

When the execution button is selected, the reconstruction computing device 45 changes the setting of the reconstruction conditions using the input content. Specifically, under the conditions in which the reconstruction FOV becomes a maximum (FOV1) (for example, the maximum FOV size is 500 mm and the reconstruction center position is a center position of rotation), the reconstruction computing device 45 generates a reconstruction image (IMAGE1) on the basis of the FBP method using a lamp filter which is strict in principle. In addition, although the initial image is generated using the FBP method herein, it is possible to use a known different reconstruction method without being limited to this. In this case, since the number of repetitions until the convergence in the iterative process changes according to the reconstruction method, it is preferable to use a reconstruction method capable of acquiring a reconstruction image with high likelihood for the projection data.

Figure 12:
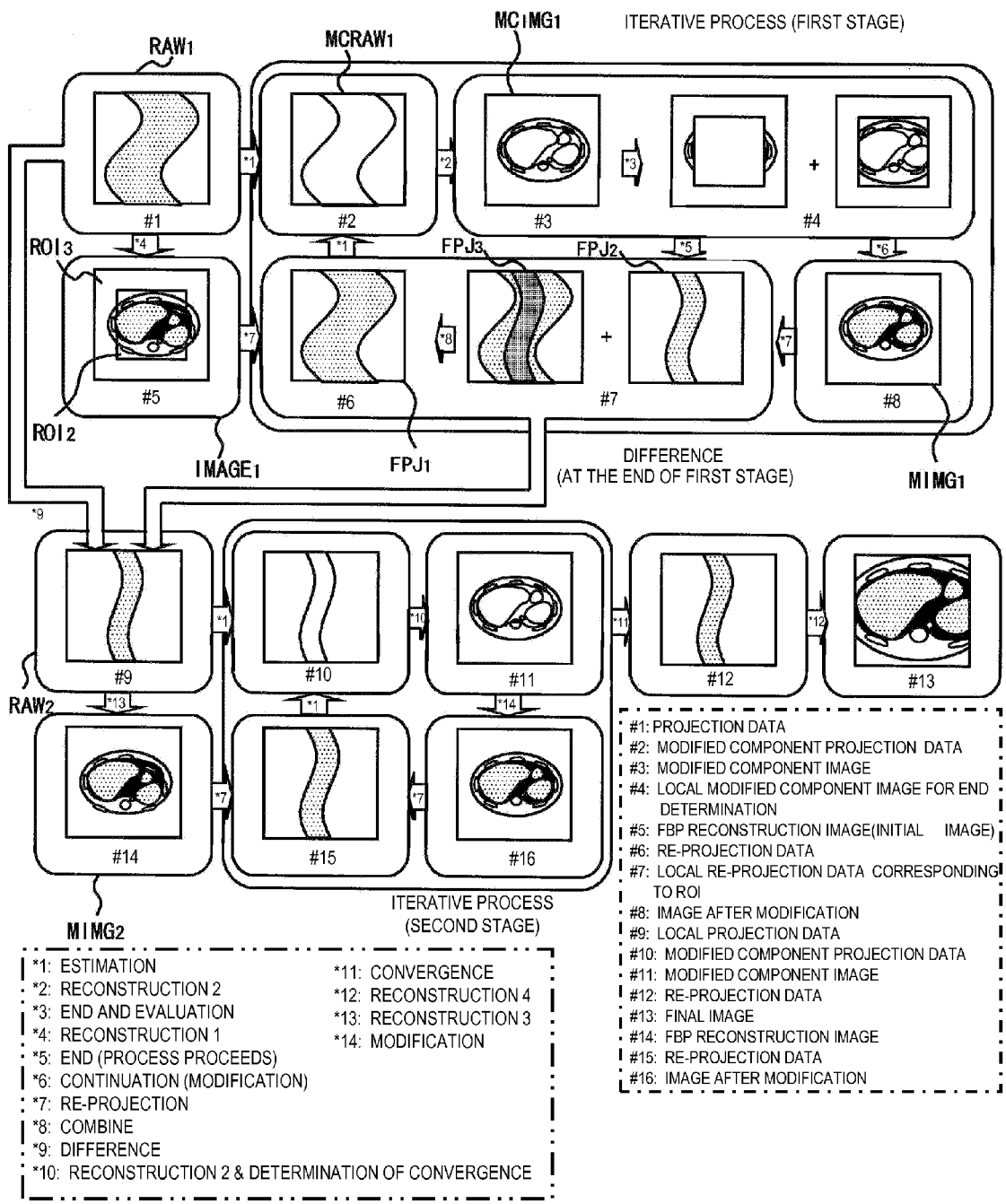
[FIG. 12]

Then, as shown in FIG. 12, the reconstruction computing device 45 divides the acquired reconstruction image of the entire scanning range (ROI1) into an image (IMAGE2), which is configured to include a region (ROI2) within the FOV2 and an image (IMAGE3), which is configured to include a region (ROI3) outside the FOV2.

Then, the reconstruction computing device 45 performs an iterative process (iterative reconstruction) with the image IMAGE1 as an initial image.

In the iterative process, the reconstruction computing device 45 performs forward projection processing of the reconstruction image (initial image) along the scanning trajectory so as to match projection data RAW1 obtained by scanning, thereby generating forward projection data FPJ1. In this case, forward projection data FPJ2 obtained by performing forward projection of the IMAGE2 and forward projection data FPJ3 obtained by performing forward projection of the IMAGE3 are separately generated in the forward projection processing, and these are combined to generate the forward projection data FPJ1 of the ROI1.

The reconstruction computing device 45 compares the generated forward projection data FPJ1 with the projection data RAW1 to generate modified component projection data MCRAW1. In this case, on the basis of a difference or ratio of the forward projection data to the projection data, the reconstruction computing device 45 calculates the modified component projection data MCRAW1 so that inconsistency between the forward projection data and the projection data is reduced (likelihood of the forward projection data becomes high). The modified component projection data MCRAW1 is treated as an error component.

The reconstruction computing device 45 generates a modified component image MCIMG1 by reconstructing the MCRAW1. In addition, the reconstruction computing device 45 generates modified image data MIMG1, which has the reduced amount of errors in the reconstruction image IMAGE1, by performing processing for weighted addition of the modified component image MCIMG1 to the reconstruction image used in the forward projection processing. As the reconstruction processing used herein, either filter-less back projection or filtered back projection may be used. In the case of the filtered back projection, for example, a lamp filter is used.

The reconstruction computing device 45 repeats the above-described processing up to the maximum number of repetitions N1 with the modified image data MIMG1 as the IMAGE1. In this case, the reconstruction computing device 45 evaluates the regions of ROI2 and ROI3 in the modified component image MCIMG1 every loop of iteration, and ends the iteration even if the number of repetitions does not reach N1 when the convergence conditions are satisfied in one of the regions.

The above is the first-stage iterative process.

In one of the regions, for example, when the ROI3 satisfies the convergence conditions in the first-stage iteration, the process proceeds to the second-stage processing.

In the second-stage processing, first, the reconstruction computing device 45 generates local projection data RAW2 equivalent to the ROI2 region by subtracting the forward projection data FPJ3 of the ROI3 obtained last from the projection data RAW1. In addition, the FPJ1 or the FPJ2 is reconstructed in the reconstruction FOV2 to obtain a reconstruction image MIMG2. Then, the iterative reconstruction is performed again under the conditions of the reconstruction FOV2 using the local projection data RAW2 and the modified image data MIMG2.

Specifically, using the RAW2 as projection data and the MIMG2 as an initial image, the iterative process is performed in the same manner as described above under the conditions of the maximum number of repetitions N2, the number of subsets SUB2, and the convergence conditions CC2.

Then, the reconstruction computing device 45 reconstructs the forward projection data obtained finally under the reconstruction conditions RCND, thereby obtaining a final reconstruction image.

As described above, in the fourth embodiment, first, the entire image is divided into the desired FOV region (ROI2) and the other region (ROI3) and the iterative process is performed over a plurality of divided stages. In the first stage, in an iterative process of the entire image, an iterative process of each region is performed for each divided region and determination regarding the convergence is performed for each region. When the convergence conditions are satisfied in one of the regions, the process proceeds to the second stage. In this second stage, forward projection data of the convergence region is fixed, and an iterative process of the remaining region is continued. Then, when the convergence conditions of the remaining region are satisfied, the iterative process is ended, and the image is reconstructed according to the desired reconstruction conditions on the basis of the forward projection data obtained last.

Therefore, also for an enlarged image from which an object protrudes due to the small image FOV, it is possible to generate a high-quality image in which cone beam artifacts or noise has been reduced by the iterative process. In addition, when performing the iterative process over a plurality of divided stages, it is possible to change the convergence conditions, the maximum number of repetitions (N1 and N2), or the number of subsets (SUB1 and SUB2) according to the stage. Accordingly, since it is possible to perform the operation more accurately for the region generated finally, the computation time can be shortened compared with a case where the entire image is calculated with high precision.

In addition, although the iterative process based on a method of modifying the image data has been described in the above embodiment, the processing of the present embodiment may also be applied to a method of modifying the projection data.

Figure 13:
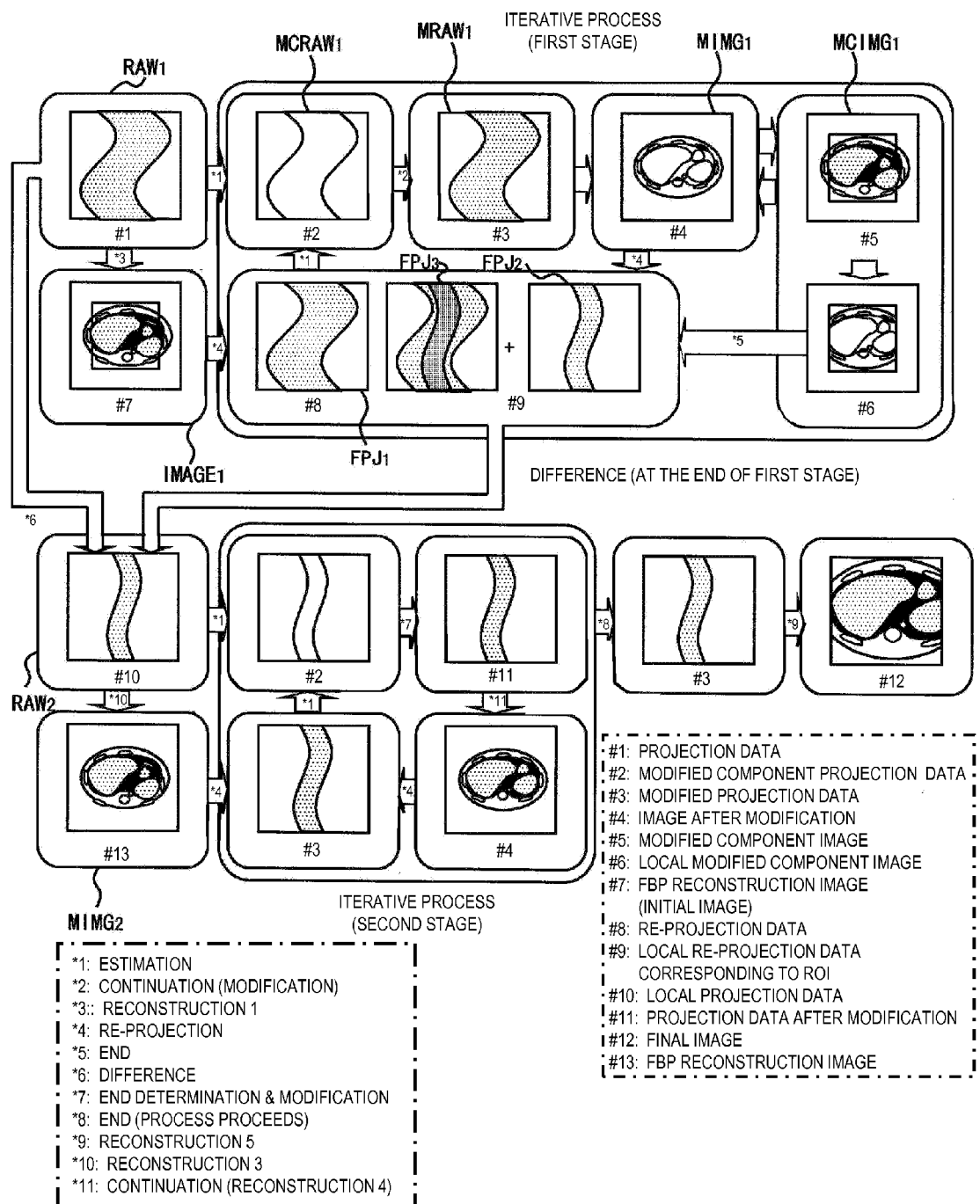
[FIG. 13]

Specifically, as shown in FIG. 13, the same modified component projection data MCRAW1 as described above is generated, and processing for weighted addition of the modified component projection data MCRAW1 to the forward projection data FPJ1 is performed to generate the modified projection data MRAW1. The modified projection data MRAW1 is reconstructed to generate the modified image data MIMG1. The modified component image MCIMG1 is generated from the difference between the modified image data MIMG1 and the IMAGE1. The above processing is repeatedly performed as one loop of the iterative process. Also when the projection data is modified in this manner, it is possible to obtain the same effect as when the image data is modified.

[Fifth Embodiment]

Next, a fifth embodiment of the present invention will be described with reference to FIG. 14.

In addition, the hardware configuration of an X-ray CT apparatus 1 of the fifth embodiment is the same as that of the X-ray CT apparatus 1 of the first embodiment shown in FIGS. 1 and 2. Therefore, explanation thereof will be omitted, and the same reference numerals are given to the same sections for the following explanation.

In the fifth embodiment, the forward projection processing and the back projection processing of the iterative process performed in the first to fourth embodiments described above have been improved.

In the iterative reconstruction, the back projection processing and the forward projection processing are important factors, and it is desirable to perform the forward projection processing at high speed and with high precision.

In many X-ray CT apparatuses, fan beam projection data is acquired by emitting fan beams spreading in a fan shape from the X-ray source 201 to the object, and reconstruction processing is performed on the basis of the fan beam projection data. In addition, also in the iterative process, when performing forward projection processing of the reconstruction image, a method of generating the fan beam forward projection data and comparing the fan beam projection data with the fan beam forward projection data is generally used.

In the forward projection for generating the fan beam projection data, however, the sampling density changes with a distance from the radiation source as shown in FIG. 14(a). Due to this, frequency information is missing. This may cause a moiré or the like.

On the other hand, in parallel beams shown in FIG. 14(b), the sampling density is equal.

In the fifth embodiment, therefore, when the X-ray projection data is fan beam projection data obtained by scanning using fan beams, the reconstruction computing device 45 converts the fan beam projection data into parallel beam projection data. In addition, when performing the forward projection processing in the iterative process, a target image is re-projected in the same beam path as for the above parallel beam projection data, and the parallel beam projection data and the parallel beam forward projection data are compared with each other. In addition, back projection of the parallel beam projection data is performed along this beam trajectory. In addition, when generating modified component projection data from projection data and forward projection data, parallel-beam-shaped modified component projection data is generated using parallel beam projection data and parallel beam forward projection data.

As described above, in the fifth embodiment, parallel beam projection data is generated from the fan beam projection data and the forward projection processing and the back projection processing are performed such that the parallel beam projection data and the beam trajectory match each other in each of the first to fourth embodiments described above. In this manner, it is possible to solve problems of a moiré due to non-uniform sampling density occurring in the fan beam forward projection data.

While the preferred embodiments of the X-ray CT apparatus related to the present invention have been described above, the present invention is not limited to the above embodiments. For example, although the gantry type X-ray CT apparatus has been described in the above embodiments, a C-arm type X-ray CT apparatus may be used. In addition, it is apparent to those skilled in the art that various changes and modifications can be made within the range of the technical idea disclosed in this specification, and it should undoubtedly be understood that they also belong to the technical range of the present invention.

REFERENCE SIGNS LIST

1: X-ray CT apparatus
2: scanner
21: central control unit
201: X-ray generator (X-ray source)
205: X-ray detector
3: bed
4: operation unit 41: display device
42: input device
43: storage device
44: computing device
45: reconstruction computing device
46: image processing device
6: object
50: initial image
51: bed region
52: object region
53: other region (air region)

The invention claimed is:

1. A reconstruction computing device comprising:
dividing means configured to group pixels of an initial image, which is reconstructed on a basis of X-ray projection data obtained by scanning an object, into plural subsets;
setting means configured to set reconstruction conditions including at least convergence conditions for each of the plural subsets divided by the dividing means;
reconstruction means configured to update estimation images by performing iterative reconstruction under the reconstruction conditions set by the setting means for each of the plural subsets divided by the dividing means, and to fix estimation images or forward projection data of a subset in which the convergence conditions are satisfied, until other subsets satisfy the convergence conditions; and
conversion means configured to convert fan beam projection data into parallel beam projection data when the X-ray projection data obtained by scanning the object is fan beam projection data,
wherein, when performing forward projection processing, the reconstruction means re-projects a target image in the same beam path as for the parallel beam projection data.

2. The reconstruction computing device according to claim 1,
wherein, when grouping pixels of the initial image into the plural subsets, the dividing means performs division according to estimated required resolution, convergence, or an amount of features regarding a shape of a region corresponding to pixels in the subset.

3. The reconstruction computing device according to claim 1,
wherein the subset is configured to include pixels corresponding to at least an object region, a bed region, and other regions.

4. The reconstruction computing device according to claim 1, further comprising:
lower subset dividing means configured to group pixels, which are included in subsets divided by the dividing means, into lower subsets each having a predetermined number of pixels or less,
wherein the reconstruction means performs forward projection processing and back projection processing in the iterative reconstruction collectively for each of the lower subsets.

5. A reconstruction computing device comprising:
dividing means configured to group pixels of an initial image, which is reconstructed on a basis of X-ray projection data obtained by scanning an object, into plural subsets;
setting means configured to set reconstruction conditions including at least convergence conditions for each of the plural subsets divided by the dividing means;
reconstruction means configured to update estimation images by performing iterative reconstruction under the reconstruction conditions set by the setting means for each of the plural subsets divided by the dividing means, and to fix estimation images or forward projection data of a subset in which the convergence conditions are satisfied, until other subsets satisfy the convergence conditions;
lower subset dividing means configured to group pixels, which are included in subsets divided by the dividing means, into lower subsets each having a predetermined number of pixels or less,
wherein the reconstruction means performs forward projection processing and back projection processing in the iterative reconstruction collectively for each of the lower subsets;
effective channel range calculation means configured to calculate involved channels, which are involved in each lower subset in the forward projection processing, and also calculate channels within a maximum width of the involved channels in all views as an effective channel range; and
shift amount calculation means configured to calculate an amount of shift of the effective channel range in a channel direction in each view in order to match the center of the effective channel range in each view to a center of all channels,
wherein, when performing forward projection processing, the reconstruction means holds forward projection data for the effective channel range of an observed lower subset, and
when performing back projection processing, the reconstruction means shifts the forward projection data for the effective channel range of the observed lower subset to an original channel position on a basis of the calculated amount of shift, compares the forward projection data with projection data which is a target of comparison to estimate a modified component, and then calculates back projection data of the observed lower subset.

6. A reconstruction computing method comprising:
a dividing step of grouping pixels of an initial image, which is reconstructed on a basis of X-ray projection data obtained by scanning an object, into plural subsets;
a setting step of setting reconstruction conditions including at least convergence conditions for each of the plural divided subsets;
a reconstruction step of updating estimation images by performing iterative reconstruction under the reconstruction conditions set in the setting step for each of the plural subsets, and fixing estimation images or forward projection data of a subset in which the convergence conditions are satisfied, until other subsets satisfy the convergence conditions;
a conversion step configured to convert fan beam projection data into parallel beam projection data when the X-ray projection data obtained by scanning the object is fan beam projection data,
wherein, when performing forward projection processing, the reconstruction step re-projects a target image in the same beam path as for the parallel beam projection data.

7. An X-ray CT apparatus comprising:
a scanner which emits X-rays to an object from a plurality of angle directions around the object and collects X-ray projection data transmitted through the object; and
a reconstruction computing device which reconstructs an X-ray CT image on the basis of the X-ray projection data collected by the scanner, wherein the reconstruction computing device includes:
dividing means configured to group pixels of an initial image, which is reconstructed on a basis of the X-ray projection data, into plural subsets;
setting means configured to set reconstruction conditions including at least convergence conditions for each of the plural subsets divided by the dividing means;
reconstruction means configured to update estimation images by performing iterative reconstruction under the reconstruction conditions set by the setting means for each of the plural subsets divided by the dividing means, and to fix estimation images or forward projection data of a subset in which the convergence conditions are satisfied, until other subsets satisfy the convergence conditions; and
conversion means configured to convert fan beam projection data into parallel beam projection data when the X-ray projection data obtained by scanning the object is fan beam projection data,
wherein, when performing forward projection processing, the reconstruction means re-projects a target image in the same beam path as for the parallel beam projection data.

* * * * *